(12) United States Patent
Howard

(10) Patent No.: US 6,946,286 B2
(45) Date of Patent: Sep. 20, 2005

(54) METHOD AND APPARATUS FOR DETECTING DNA HYBRIDIZATION

(75) Inventor: John K. Howard, Saratoga, CA (US)

(73) Assignee: Matsushita Electric Industrial Co., Ltd., Osaka (JP)

(*) Notice: Subject to any disclaimer, the term of this patent is extended or adjusted under 35 U.S.C. 154(b) by 511 days.

(21) Appl. No.: 10/141,345

(22) Filed: May 9, 2002

(65) Prior Publication Data

US 2003/0211479 A1 Nov. 13, 2003

(51) Int. Cl.[7] .............................................. C12M 1/34
(52) U.S. Cl. ........................ 435/287.2; 435/288.7; 422/82.08; 250/553; 250/461.1; 356/435; 257/292
(58) Field of Search ...................... 435/6, 287.2, 288.7, 435/808; 422/82.05, 82.07, 82.08; 250/553, 461.1, 462.2, 462.1; 356/246, 432, 435, 440; 257/84, 292

(56) References Cited

U.S. PATENT DOCUMENTS

| | | |
|---|---|---|
| 5,578,832 A | 11/1996 | Trulson et al. |
| 5,631,734 A | 5/1997 | Stern et al. |
| 6,197,503 B1 * | 3/2001 | Vo-Dinh et al. ............... 435/6 |
| 6,251,685 B1 * | 6/2001 | Dorsel et al. ............... 436/172 |
| 6,458,547 B1 * | 10/2002 | Bryan et al. ................. 435/7.1 |

* cited by examiner

Primary Examiner—William H. Beisner
(74) Attorney, Agent, or Firm—McDermott Will & Emery LLP

(57) ABSTRACT

An apparatus for identifying an unknown DNA sample. The apparatus includes a plurality of detection nodes, each of which is operable for allowing an interaction between a known DNA sample and an unknown DNA sample, and for generating an output signal if hybridization occurs between the known DNA sample and the unknown DNA sample. The apparatus further includes a decoder operative for receiving an input signal indicative of which of the plurality of detection nodes should be selected for processing and for outputting control signals which operate to activate the selected detection node. Further, each of the detection nodes includes a light source and a photodetection circuit. The photodetection circuit has a conductance value which varies if hybridization occurs between the known DNA sample and the unknown DNA sample deposited in the detection node. This change in conductance value is utilized to generate the output signal which indicates that hybridization has occurred.

20 Claims, 9 Drawing Sheets

METHOD AND APPARATUS FOR DETECTING DNA HYBRIDIZATION

FIELD OF THE INVENTION

This invention relates generally to a system and method of detecting interactions between analyte molecules, and more particularly, to a system and method for determining DNA hybridization.

BACKGROUND OF THE INVENTION

DNA sequencing is becoming a major factor in a number of different emerging scientific fields. For example, DNA sequencing has been utilized in an attempt to diagnosis various diseases. One known method of performing such DNA sequencing/analysis is by matching an array of known DNA sequences (referred to as probes) with an unknown target DNA. More specifically, such a process typically includes placing a number of known DNA sequences on a glass slide. Each of the known DNA sequences are placed at a specific geographic location on the glass slide. A typical glass slide may have the capability of containing 50,000 individual locations, thereby allowing for processing of 50,000 DNA sequences.

Once the known DNA probes are placed in the predetermined locations on the slide, an unknown sample of DNA is placed on the slide. After a set period of time, if the unknown sample of DNA matches any of the known DNA sequences, the unknown DNA sample will hybridize with the known DNA sequence at the given location of the known DNA sequence. Assuming there is a match, the unknown sample DNA is identified as the DNA sequence with which the hybridization occurred.

In accordance with the foregoing technique, it is necessary to determine whether hybridization has occurred as well as the specific location of the hybridization so as to allow for a correlation between the location of the hybridization and the corresponding known DNA sequence. One common method of performing this determination is by an optical detection technique. In accordance with this technique, first, after allowing sufficient time for hybridization between the known DNA sequences and the unknown sample DNA, the slide is treated such that all un-hybridized DNA are removed from the slide. Next, an optical detection technique is utilized to determine the presence of a fluorescent molecule, which is attached to each unknown DNA sequence prior to the hybridization process. Specifically, if hybridization has occurred, the fluorescent molecule (i.e., die) attached to the unknown DNA sequence will be present after the known DNA sequence has hybridized with the unknown DNA sample (if there was no match, all the known DNA sequences would be removed from the slide during the aforementioned treatment process). Accordingly, by utilizing, for example, a laser and a photo detector, it is possible to determine the presence and location of the fluorescent molecule, which identifies the sample DNA by correlating the position of the fluorescent molecule with the location of the known DNA sequences. Typically, the instrument utilized to determine the presence of the fluorescent molecule is a desktop micro-array scanner.

Specific examples of such known optical detection systems and methods are set forth in U.S. Pat. No. 5,578,832, "Method And Apparatus For Imaging A Sample On A Device" issued to Trulson et al., and U.S. Pat. No. 5,631,734, "Method And Apparatus For Detection Of Fluorescently Labeled Materials", issued to Stern et al. Both of the foregoing patents are hereby incorporated by reference. Utilizing a method similar to that described above, both of the foregoing patents employ the use of a fluorescent molecule, such as fluorophore and biotin, which is attached to the unknown DNA sequence. An optical system is then utilized to determine whether hybridization has occurred by measuring fluorescence activated between the sample DNA and the known DNA.

Notwithstanding the foregoing chemical interaction detection systems utilized to identify unknown DNA samples, problems remain. For example, the time requirements for operating the system can be exceedingly long as a typical array to be analyzed may contain on the order of 50,000 DNA samples, which need to be scanned on a one-by-one basis during processing. More specifically, as the laser light source must be positioned over each and every DNA sample to be analyzed, the simple process of continually positioning the laser over the DNA samples is considerably time consuming due to the number of samples contained in a typical array. Indeed, this problem only increases as the number of known DNA to be considered for a given testing process increases.

Accordingly, there remains a need for providing a detection system capable of identifying unknown DNA samples that eliminates the need for the optical scanner so as to allow for a reduction in both the time and cost associated with performing the analysis.

It is the object of the present invention to correct the foregoing deficiencies in the prior art.

SUMMARY OF THE INVENTION

In general, the present invention relates to a DNA detection system that provides for identification of the unknown DNA in an electronic manner. The DNA detection system of the present invention eliminates the need for utilizing an optical scanner during the detection process, and as a result, allows for a relatively fast and mobile identification of any matching DNA samples with an associated reduction in the cost and complexity of the analyzing process.

In a first exemplary embodiment, the present invention relates to an apparatus for identifying an unknown DNA sample. The apparatus comprises a plurality of detection nodes, each of which is operable for allowing an interaction between a known DNA sample and an unknown DNA sample, and for generating an output signal if hybridization occurs between the known DNA sample and the unknown DNA sample. The apparatus further comprises a decoder operative for receiving an input signal indicative of which of the plurality of detection nodes should be selected for processing and for outputting control signals which operate to activate the selected detection node. Further, each of the detection nodes includes a light source and a photodetection circuit. The photodetection circuit has a conductance value which varies if hybridization occurs between the known DNA sample and the unknown DNA sample deposited in the detection node. This change in conductance value is utilized to generate the output signal which indicates that hybridization has occurred.

As described in further detail below, the present invention provides significant advantages over the prior art. Most importantly, the method and system of detecting/identifying unknown DNA of the present invention allows for the elimination of the need for utilizing an optical scanner during the detection process, and allows for real-time detection of unknown DNA. As such, the present invention allows for a reduction in the overall cost and time associated with performing the detection analysis.

DETAILED DESCRIPTION OF THE DRAWINGS

The following detailed description relates to a novel DNA detection system that allows for electronic detection/identification of unknown DNA. The description of the exemplary embodiments of the system sets forth numerous specific details regarding the configuration of the system. It will be obvious, however, to one skilled in the art that these specific details need not be employed to practice the present invention. Clearly, other configurations and implementations of the DNA detection system are possible.

Figure 1:
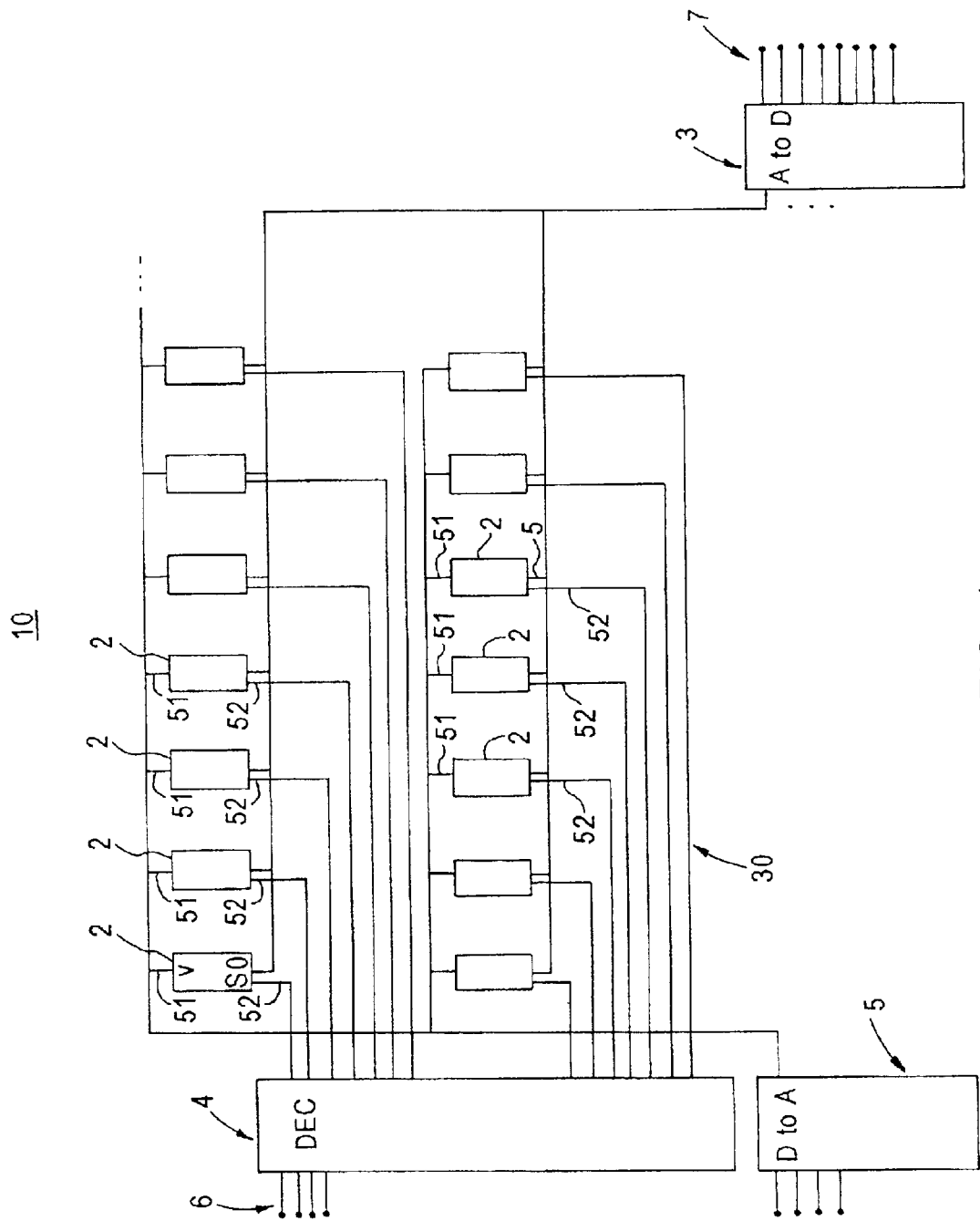
FIG. 1 is a block diagram of an exemplary embodiment of the DNA detection system in accordance with the present invention.

FIG. 1 illustrates a block diagram of an exemplary embodiment of the DNA detection system 10 in accordance with the present invention. Referring to FIG. 1, the system 10 comprises a plurality of addressable detection nodes 2, a node selection decoder 4, a D/A converter 5 and an A/D converter 3. As explained in further detail below, each of the plurality of detection nodes 2 has an identical structure and is capable of comparing a known DNA sample with an unknown DNA and outputting an electronic signal if the given DNA sample and unknown DNA hybridize (i.e., match). Each addressable detection node 2 comprises three signal lines coupled thereto. The first is a variable input voltage signal line 51 for receiving a voltage signal output by D/A converter 5. A variable voltage source (not shown) is coupled to the input of the D/A converter 5 and is utilized to vary the input voltage applied to each addressable detection node 2. The level of the voltage input into the addressable detection nodes 2 is determined by empirical methods and varies depending on the particular DNA assay being analyzed.

Figure 2:
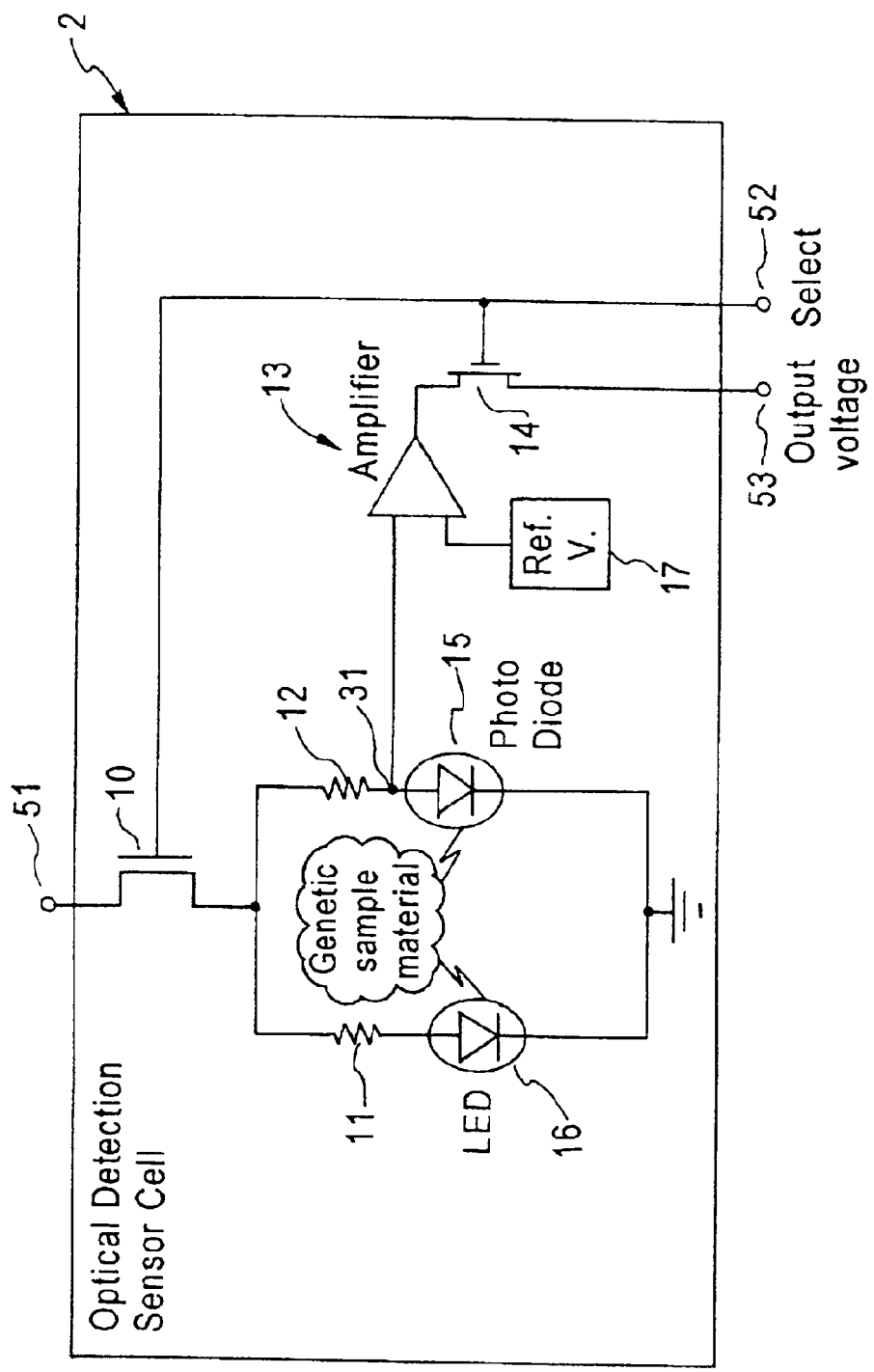
FIG. 2 is an exemplary schematic diagram illustrating one embodiment of a detection node utilized on the DNA detection system illustrated in FIG. 1.

The second signal line is the select line 52, which as explained in conjunction with FIG. 2 is utilized to select a given addressable detection node 2 for analysis. As shown, each select line 52 is also coupled to the output of the node selection decoder 4. In the preferred embodiment, node selection decoder 4 functions to activate a single select line 52 at a time so as to allow for analysis of the corresponding detection node 2. The detection node 2 to be selected is determined by the digital control signal 6 coupled to the input of the node selection decoder 4. The digital control signal 6 is generated by a computer/controller (not shown). As stated, the node selection decoder 4 is utilized to select any one of the detection nodes 2 by inputting a signal corresponding to the address of the desired detection node 2 into the node selection decoder 4. During operation, for example, the selection node decoder 4 may be controlled so as to sequentially activate each detection node 2 so as to allow for determination of whether or not the known DNA and the unknown DNA in the given detection node 2 hybridized (i.e., match).

The third signal line 53 is an output line which functions to couple the output signal generated by the given detection node 2 to the A/D converter 3. As explained in further detail below, the output signal of a given detection node 2 exhibits a first voltage level if the known DNA and the unknown DNA in the given detection node 2 hybridize, and exhibits a second voltage level if the known DNA and the unknown DNA do not hybridize. The output line 53 of a given detection node 2 is activated upon selection of the given detection node 2 by the selection node decoder 4. Accordingly, in the preferred embodiment, only one output signal line 53 is active at a time. The output of the A/D converter 3 is coupled to a computer/controller (not shown) for analysis and recordation of the data. For example, assuming the voltage level of the output signal of detection node "X" indicates hybridization has occurred, as the identification of the known DNA deposited in detection node "X" is recorded and stored in memory, upon receiving the signal indicating hybridization has occurred, the computer/controller retrieves the data associated with detection node "X", which identifies the known DNA contained in detection node "X", and labels the unknown DNA placed in detection node 2 equal to the known DNA.

FIG. 2 is an exemplary schematic diagram illustrating one embodiment of a detection node 2, which is also referred to as a biosensor cell. Referring to FIG. 2, each biosensor cell 2 includes resistors R11 and R12, a light source 16 (e.g., an LED), a photodiode 15, a differential amplifier 13 and transistors 10 and 14 which function to activate the given biosensor cell 2 and to couple the output of the biosensor cell 2 to the A/D converter 3. The operation of the biosensor cell 2 is as follows.

First, in order to select/activate a given biosensor cell 2, the corresponding selection line 52 must be made active by the selection node decoder 4. Activation of the selection line 52 functions to turn on transistors 10 and 14. As a result, the voltage signal "V" on the first signal line 51 is coupled to the resistors R11 and R12 as well as the LED 16 and the photodiode 15. In addition, the output of the differential amplifier 13 is coupled to the output signal line 53. Upon application of the voltage signal "V", the LED 16 is activated and emits light. As explained below in further detail, in the event there is a match between the known DNA and the unknown DNA in the given biosensor cell 2, the light emitted from the LED 16 is incident on a fluorescent tag attached to the unknown DNA. As a result, the fluorescent tag emits light (i.e., fluoresces) which is received by the photodiode 15. As is known, when the light incident on the photodiode 15 increases, the current flowing through the photodiode 15 increases. The increase in current flow through the photodiode 15 causes an increase in current flow through resistor 12, thereby causing an increase in the voltage drop across resistor 12. The increase in the voltage drop across resistor 12 results in voltage drop at node 31. In other words, the photodiode 15 and the resistor 12 effectively form a voltage divider circuit, which exhibits a voltage drop at node 31 when the photodiode receives light emitted by the fluorescent tag molecule (which is only generated if hybridization occurs).

The effective voltage divider circuit formed by resistor R12 and the photodiode 15 generates a first reference voltage at node 31, which is coupled to one input of the differential amplifier 13. The second input to the differential amplifier 13 is a second reference voltage 17, which can be, for example, a predetermined fixed voltage source. It is noted that while a LED 16 and a photodiode 15 have been illustrated in the exemplary embodiment of FIG. 2, it is possible to practice the present invention utilizing any suitable light emitting source and any suitable light detection source (e.g., a CCD array, a CMOS sensor, etc.) having an electrical characteristic which varies in accordance with the amount of received light. Furthermore, as explained below in further detail with reference to FIG. 3, in the preferred embodiment, both the LED 16 and the photodiode 15 are formed in a monolithic structure (i.e., a single integrated circuit). Indeed, in the preferred embodiment, a substantial plurality of biosensor cells 2 are formed in a single integrated circuit chip. Resistors R11 and R12 are fixed resistors of equal value and are fabricated utilizing standard semiconductor processing techniques.

As explained below in further detail, each biosensor cell 2 is formed such that known DNA is placed on a surface of the substrate in which the biosensor cell 2 is formed. In addition, the structure of the biosensor cell 2 is fabricated so as to allow for receipt of unknown DNA on the same surface. The structure of the substrate is such that the light emitted from the LED 16 is incident on the DNA disposed on the substrate, and assuming a match, the light generated by the fluorescent tag molecule attached to the unknown DNA is received by the photodiode 15.

It is noted that the delivery of the known DNA and the unknown DNA to the substrate surface can be accomplished utilizing various capillary designs for transporting such material as is well known by those of skill in the art. Indeed, as the preferred embodiment of the present invention entails forming the detection system on a single semiconductor chip, in one embodiment, after formation of the transistors and the other circuitry noted above, an additional layer is formed on the semiconductor structure which includes the necessary capillary design so as to allow the unknown DNA to be delivered to the substrate surface. As explained below, in the preferred embodiment, the known DNA is deposited on the surface of the substrate during the formation of the device. Alternatively, the known DNA and the unknown DNA can both be delivered to the substrate surface subsequent to the formation of the device, by capillary structures included in the additional layer on the semiconductor structure.

Figure 3:
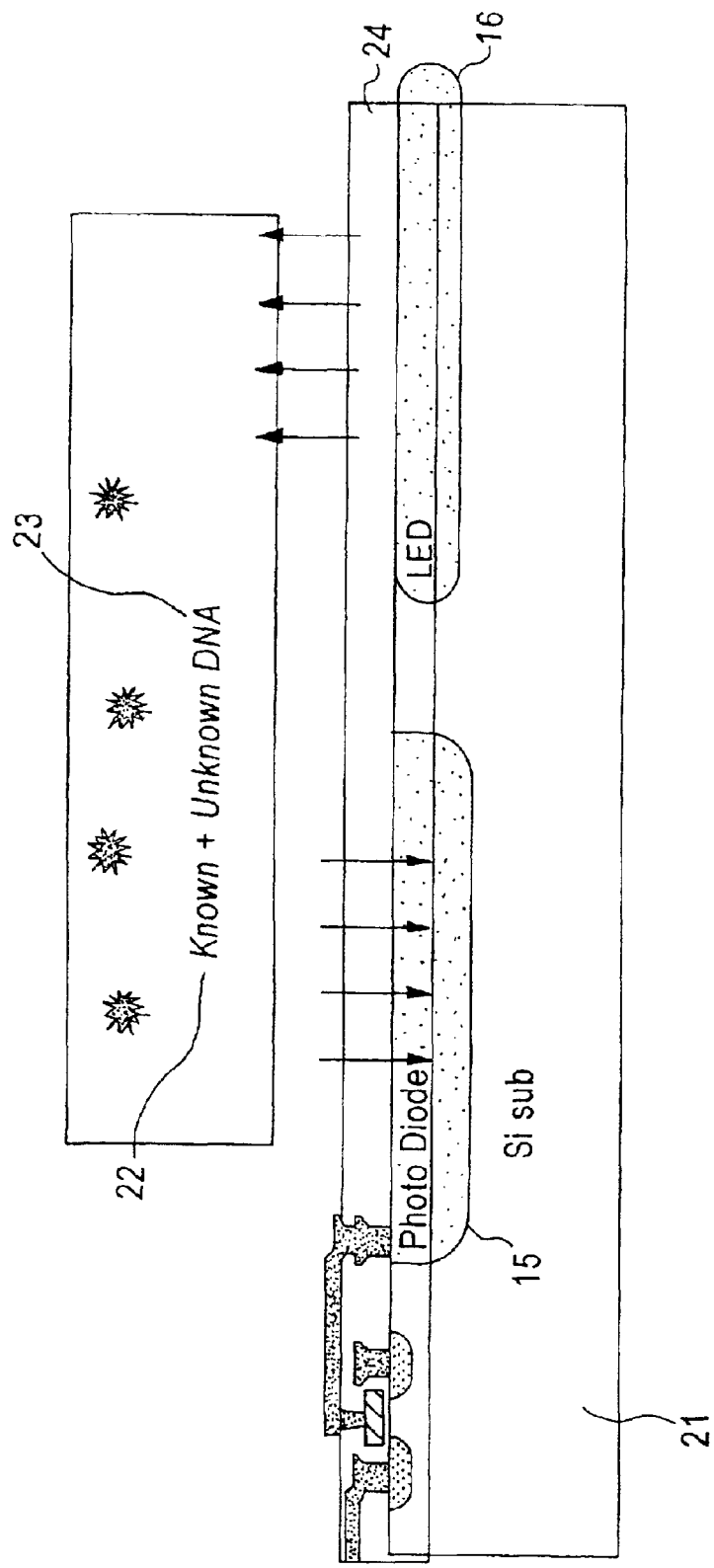
FIG. 3 illustrates an exemplary embodiment of the formation of the LED and photodiode in a semiconductor substrate.

FIG. 3 is a cross-sectional view of a substrate illustrating an exemplary formation of the LED 16 and the photodiode 15 in accordance with the present invention. It is noted that resistors R11 and R12 are not illustrated in FIG. 3. However, in practice, the resistors would also be formed in the same semiconductor device, along with the other components forming the biosensor 2. As stated above, numerous biosensors would be formed in a single integrated circuit chip. Referring to FIG. 3, standard CMOS processing is utilized to form the LED 16 and the photodiode 15 in a silicon substrate 21. Of course, any suitable processing technology can be utilized. An isolation layer 24, for example, SiO2, is formed over the upper surface of the semiconductor substrate 21 in which the LED 16 and the photodiode 15 are formed. It is noted that any suitable isolation layer can be utilized, as long as the isolation layer allows for the transmission of light.

As mentioned above, in one embodiment, the known DNA is placed in a plurality of test sites during the formation of the device. In the present embodiment, each biosensor cell 2 has a sole test site, which corresponds to the area illustrated in FIG. 3. As such, after the formation of the isolation layer 24, a robotic spotter utilizing a normal pen or ink jet technology can be utilized to apply known DNA 22 to the surface of the isolation layer 24 (also referred to as the upper surface of the substrate) located above the LED 16 and photodiode 15. It is preferable that the amount of the known DNA 22 placed on the surface of the isolation layer 24 be sufficient to entirely cover the LED 16 and the photodiode 15. As noted above, after deposition of the known DNA 22 on the substrate, an additional layer 70 (see, FIG. 6) is formed (e.g., bonded) on the semiconductor structure comprising the isolation layer 24 and the substrate 21. The additional layer 70 includes the necessary capillary design 71 so as to allow the unknown DNA 23 to be delivered to the substrate surface and contact the known DNA 22.

Figure 4:
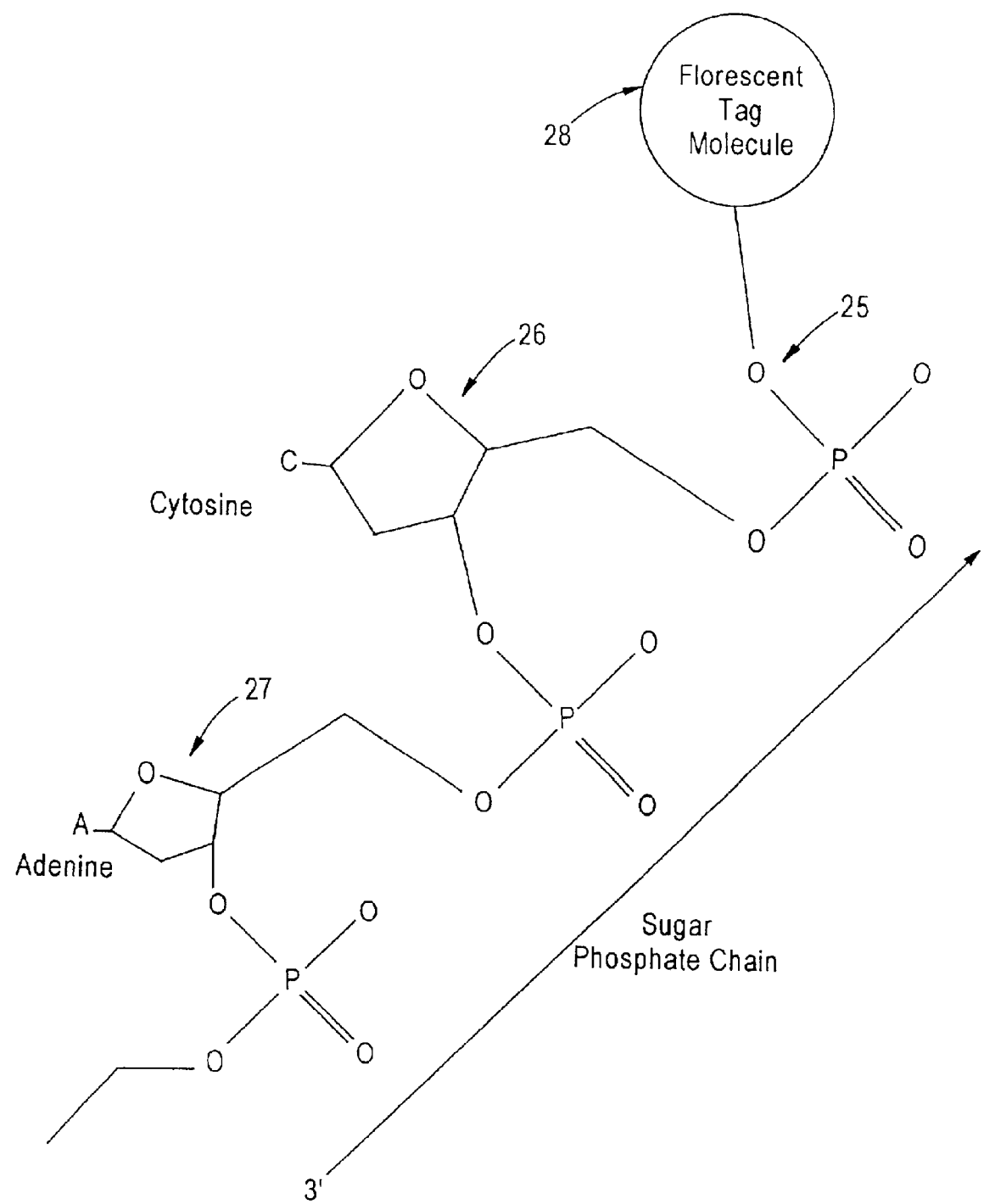
FIG. 4 is an exemplary molecular diagram illustrating the attachment of a fluorescent tag molecule to an unknown DNA molecule.

In accordance with the present embodiment, each unknown DNA sample 23 to be analyzed in a given test site (i.e., biosensor cell 2) has a fluorescent tag molecule attached thereto. As explained in further detail below, in the event there is a match between the known DNA 22 and the unknown DNA 23, the DNA strands hybridize and remain present within the biosensor cell 2 along with the fluorescent tag molecule on the surface of the isolation layer 24. As such, when the light generated by the LED 16 is incident on the fluorescent tag molecule, the molecule emits light which is detected by the photodiode 15. As explained below, it is this emission of light by the fluorescent tag molecule and the detection of this light by the photodiode 15 that is utilized to indicate a match (i.e., hybridization) has occurred. FIG. 4 illustrates an exemplary molecular diagram illustrating the attachment of a fluorescent tag molecule to an unknown DNA sample molecule 23. An example of a fluorescent tag molecule is Cy-duTP. Of course, any other suitable fluorescent tag molecule can be utilized. It is noted that the unknown DNA sample 23 illustrated in FIG. 4 is a sugar phosphate chain.

The specific operation of the biosensor cell of the present invention will now be discussed. Prior to the deliver of the unknown DNA 23 to the substrate surface 24 of a given biosensor cell 2, the light received by the photodiode 15 is approximately equal to some predetermined value (e.g. zero), and therefore the voltage level at node 31 is a known value. This predetermined value corresponds to the value of light received by the photodiode 15 when the circuit is in operation, but without the occurrence of hybridization. It is noted that the actual value of the voltage level will vary depending on the process technology and type of LED 16 and photodiode 15 utilized. Once the steady state voltage level at node 31 is determined/set, the reference voltage 17 is selected such that the output of the differential amplifier 13 is a set value (e.g., zero). In other words, the reference voltage 17 can be selected to be substantially equal to the steady state voltage at node 31.

Once the unknown DNA 23 is supplied to the surface of the substrate 24 so as to contact the known DNA 22, if the unknown DNA 23 matches the known DNA 22 sample already deposited on the surface of the substrate 24 in the given biosensor cell 2, the known DNA sample 22 hybridizes to the unknown DNA 23, and the highly fluorescent molecule remains on the surface of the substrate 24 of the given biosensor cell 2. It is noted that the known DNA 22 and the unknown DNA 23 are allowed a predetermined amount of time to hybridize and then the substrate is treated so as to remove all unhybridized DNA. As a result, only if there is a match between the known DNA 22 and the unknown DNA 23 will any DNA remain on the substrate surface 24 of the biosensor cell 2 after the treatment process.

It is noted that the time period for allowing the DNA to hybridize prior to treating the substrate to remove all non-hybridized DNA typically varies from 1–24 hours. In the given embodiment, the non-hybridized DNA is removed by depositing an enzyme solution (e.g., dnase) on the chip, which functions to eliminate the non-hybridized DNA (i.e., single strand DNA). The enzyme dos not attach the double stranded (i.e., matched) DNA.

In the event hybridization occurs between a known DNA sample 22 and an unknown DNA sample 23 deposited in a given biosensor cell 2, the fluorescent tag molecule remains present in the biosensor cell 2 after the treatment process. Thus, the presence of the fluorescent tag molecule indicates that hybridization has occurred, or in other words, a match in DNA has occurred. Importantly, the presence of the fluorescent tag molecule also results in a change of light received by the photodiode 15, which is utilized to indicate the detection of the match between the known and unknown DNA.

More specifically, as noted above, when a given biosensor 2 is active (i.e., selected by the decoder 4), the LED 16 and the photodiode 15 are active. In the event hybridization has not occurred in the selected biosensor cell 2, the voltage level at node 31 is substantially equal to the predetermined level noted above (e.g., zero). However, if hybridization has occurred, the fluorescent tag molecule, which is now present in the biosensor cell 2, receives light from the LED 16. This light causes the fluorescent tag molecule to emit light, which is received by the photodiode 15. As noted above, upon receipt of the light emitted from the fluorescent tag molecule, the current output by the photodiode 15 increases and the voltage drop across resistor 12 increases, thereby causing a decease in the voltage level at node 31. The change in voltage at node 31 generates a difference between the voltage of the node 31 and the second reference voltage 17 coupled to the other input of differential amplifier 13. This difference in voltage is amplified by differential amplifier 13 and output to the A/D converter 3, and coupled to a data analyzer/computer (not shown) for processing. In particular, when the difference voltage output by the differential amplifier 13 exceeds some predetermined threshold value, the unknown DNA input into the given biosensor cell 2 is deemed to be the same as the known DNA contained in the given biosensor cell 2. Thus, as the known DNA supplied to the given biosensor cell 2 is known, upon detection of a match, the previously unknown DNA supplied to the given biosensor cell is identified as being the same as the known DNA.

It is noted that when selecting the value of the second reference voltage 17, the important factor is that the resulting difference in the voltage level at node 31, when the fluorescent tag molecule reflects light (i.e., a match has occurred) and when no light is generated by a fluorescent tag molecule (i.e., no match has occurred), is substantial enough so as to generate a detectable difference at the output of differential amplifier 13. It is further noted that the amount of DNA and fluorescent tag molecules to be deposited on the substrate surface of the biosensor cell necessary to generate a sufficient amount of light to be detected by the photodiode 15 can be determined by empirical methods and will likely vary depending on the given DNA and fluorescent tag molecules under consideration, as well as the type of LED and photodiode utilized.

Figure 5:
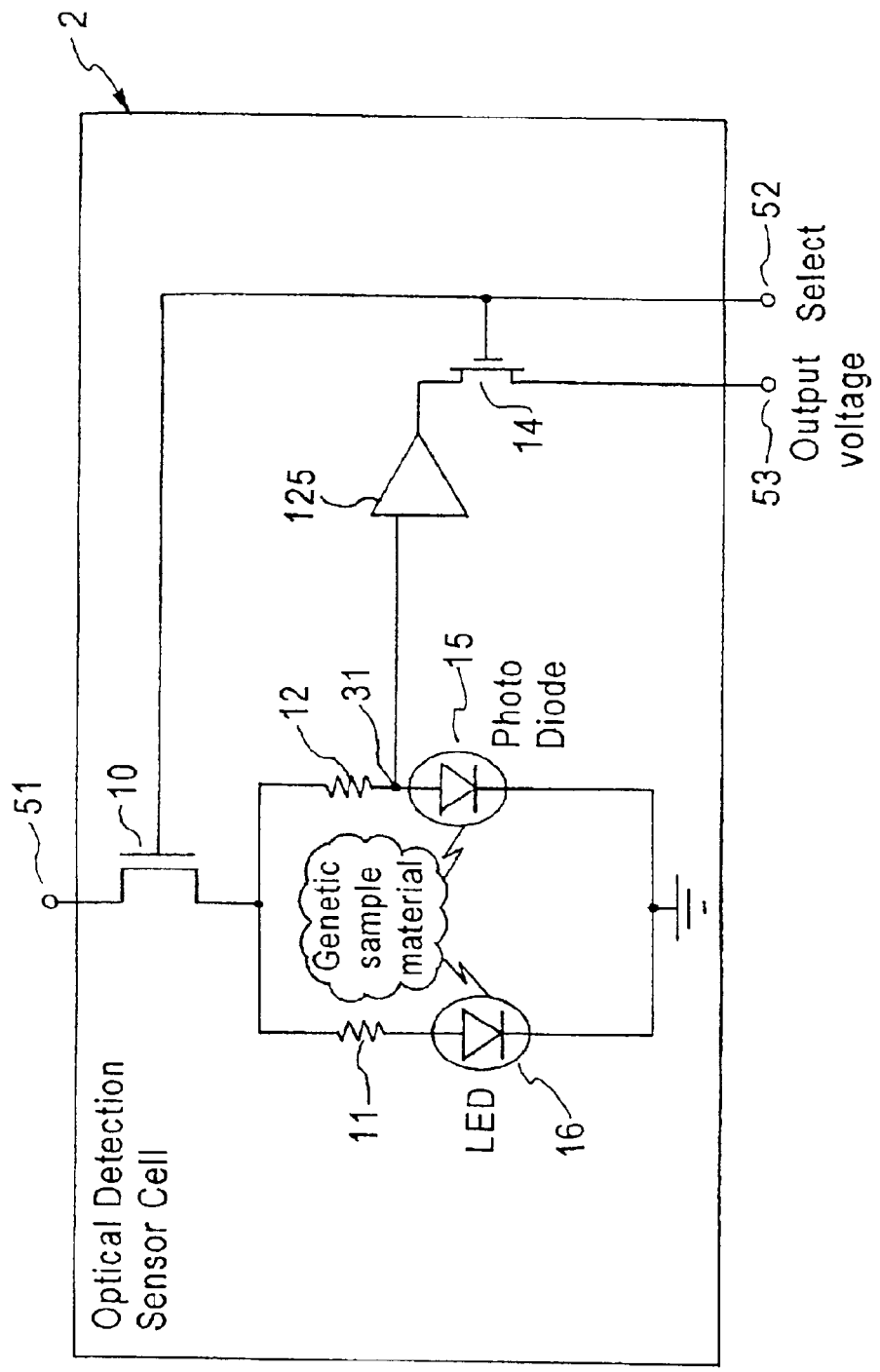
FIG. 5 is an exemplary schematic diagram illustrating a second embodiment of a DNA detection system in accordance with the present invention.

FIG. 5 illustrates an exemplary schematic diagram of a second embodiment of a DNA detection system in accordance with the present invention. Referring to FIG. 5, in the second embodiment the biosensor cell 200 is modified such that the differential amplifier 13 is eliminated from the design and replaced with a sense amplifier 125. The remaining components contained in the biosensor cell 200 are the same as those disclosed above in FIG. 2 and they perform in the same manner as detailed above.

In accordance with the operation of the second embodiment, after formation of the biosensor cell 2 and before deposition of the unknown DNA, the current/conductance at node 31 of the biosensor cell 2 is monitored/measured by sense amplifier 125 so as to establish a known current/conductance value. Thereafter, the unknown DNA is deposited over the surface of the substrate 24 in which the LED 16 and the photodiode 15 are formed. After depositing the unknown DNA, the current at node 31 is measured again. In the event hybridization has occurred, there will be a significant increase (e.g., at least double) in the amount of current flowing through node 31. Assuming the current/conductance value is above a predefined value, which is determined utilizing the current/conductance value of node 31 prior to depositing the unknown DNA, the unknown DNA supplied to the biosensor cell 2 is deemed to match with the known DNA contained in the biosensor cell 2. It is noted that the second embodiment of the present invention is essentially monitoring the current value of the photodiode 15 to determine if a change in current value occurs upon depositing the unknown DNA. A change in the current value indicates that hybridization has occurred, and that the unknown DNA matches the DNA contained in the given biosensor cell 2. The second embodiment of the present invention advantageously allows for the elimination of the differential amplifier and the reference voltage source. In addition, the determination of a match made be made more quickly with real time monitoring of rate of change.

It is noted that in accordance with both the first and second embodiments of the present invention, the surface of the substrate 24 on which the DNA is deposited is coated with a hydrophilic material, for example, a polypeptide alled polyl, so as to allow the binding of immobilization chemistry (i.e., the binding of the DNA material to the floating gate).

Figure 6:
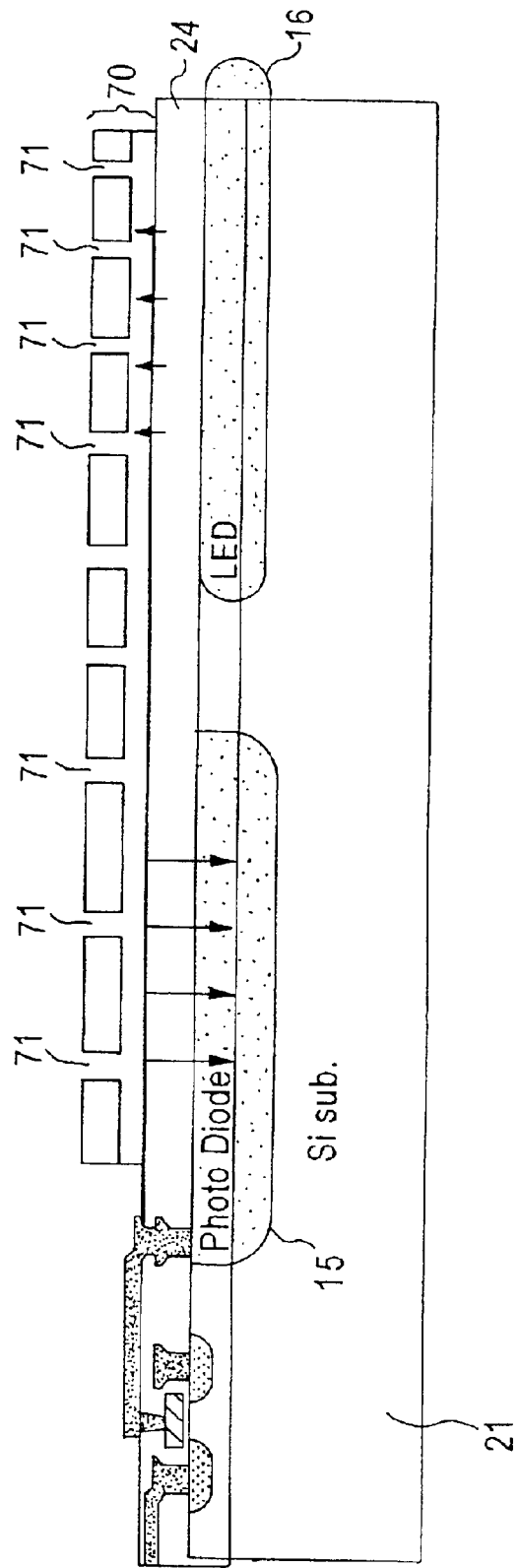
FIG. 6 illustrates an exemplary embodiment of a micromachined manifold layer comprising a plurality of capillaries, which allow for delivery of the unknown DNA sample to the substrate surface.

As stated above, in accordance with the first embodiment, once the known DNA is deposited on the substrate surface, a micro-machined manifold layer 70 is bonded to the upper surface of the semiconductor chip. Referring to FIG. 6, the micro-machined manifold layer 70 comprises a plurality of capillaries 71 (i.e., passageways), which allow for subsequent delivery of the unknown DNA sample to the substrate surface 24 of each biosensor cell 2 in the array. The design of capillary networks capable of performing this function are known in the art. In the current embodiment, the design is such that a small open area above the surface of the substrate 24 is maintained so as to allow for receipt of the unknown DNA 23 on the surface of the substrate 24. Furthermore, as a variation to the foregoing, as noted above, it is possible to design the capillary network so as to allow for the deposition of both the known DNA and the unknown DNA to the substrate surface 24 of each biosensor cell 2.

As described above, the present invention provides significant advantages over the prior art. Most importantly, the method and system of detecting/identifying unknown DNA of the present invention allows for the elimination of the need for utilizing of an optical scanner during the detection process, and allows for real-time detection of unknown DNA. As such, the present invention allows for reduction in the overall cost and time associated with performing the detection analysis.

Yet another advantage is that the system of the present invention can be implemented in a single semiconductor integrated circuit chip, and the number of biosensor cells contained on the chip can vary from chip to chip depending on the intended application. Moreover, a medical technician can simply supply the unknown DNA to the system chip and the system chip can determine if the unknown DNA matches any of the known DNA in the system chip without any further analysis or measurements being performed by the technician.

Numerous variations of the foregoing embodiments of the present invention are also possible. For example, a comparator can be included in each biosensor cell, which functions to generate an output signal only if the output of the differential amplifier is a above some predetermined level. In such an embodiment, the comparator functions to output a signal (e.g., logical "1") only if hybridization occurs between the known DNA sample and the unknown DNA.

Figure 7:
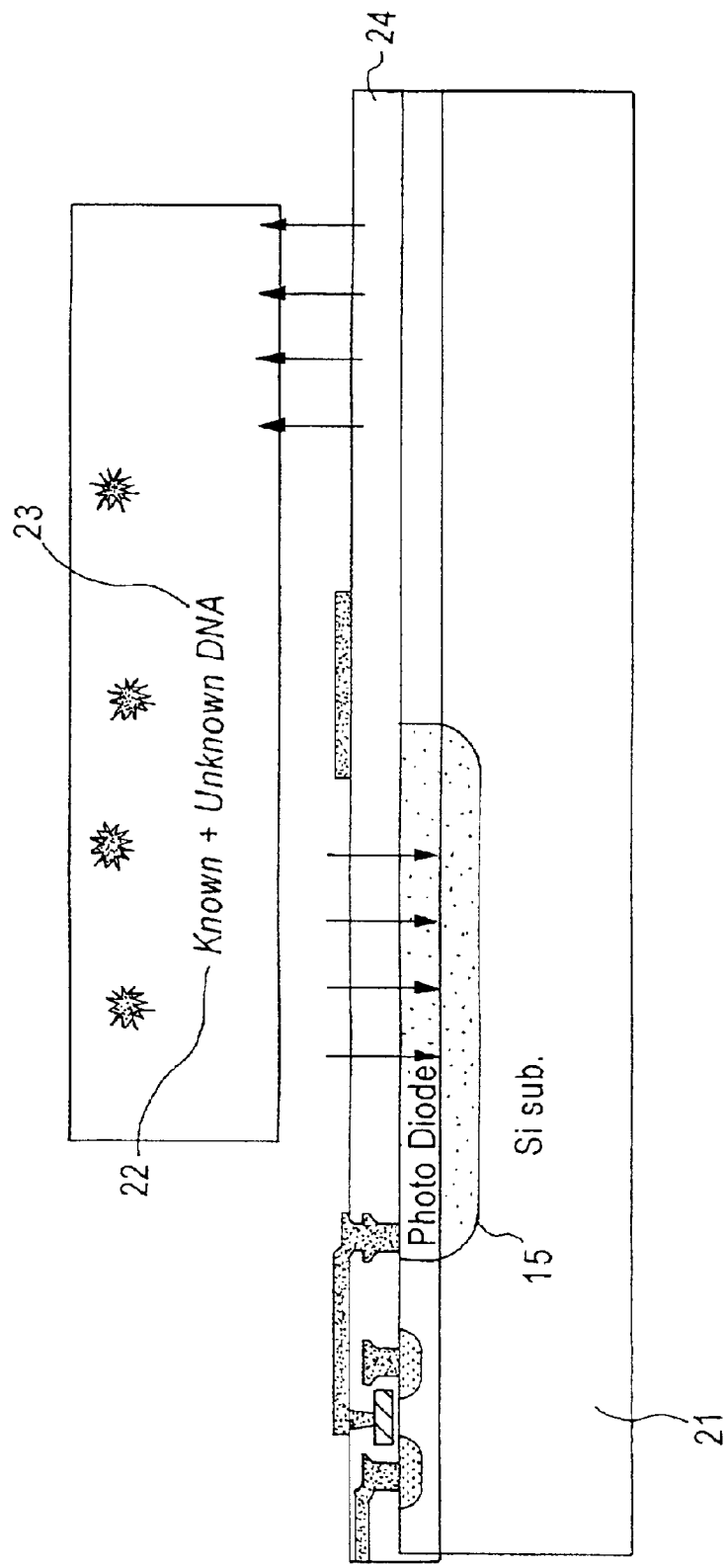
FIG. 7 illustrates a second embodiment of a biosensor cell in accordance with the present invention.

In another variation, the embodiments disclosed above are modified such that each biosensor cell contains only a photodetector. Referring to FIG. 7, the biosensor cells are formed such that each cell contains the photodetector, but omits the LED (it is noted that FIG. 7 illustrates a portion of a single biosensor cell). The remainder of each biosensor cell is formed in a similar manner to the biosensor cell disclosed above. The biosensors cells 82 are formed within the substrate so as to form an x-y array of cells 81, and so as to allow deposition of the known and unknown DNA samples to be deposited on the substrate comprising the biosensor cells. This can be accomplished, as explained above, by means of a robotic spotter. Further, the upper surface of the substrate is exposed so as to allow an excitation light to illuminate the surface of the substrate.

Figure 8:
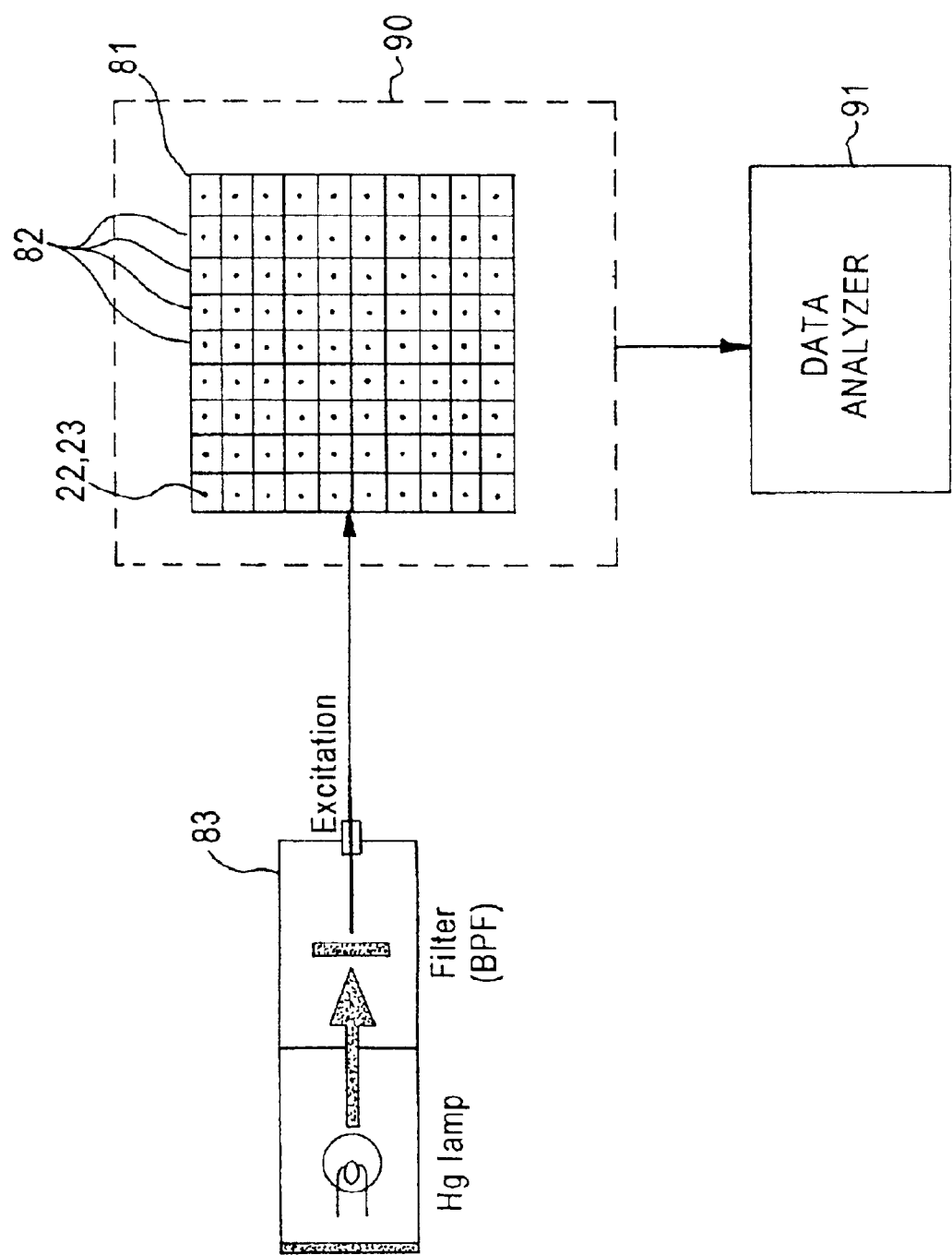
FIG. 8 illustrates a block diagram of the system of the present invention utilizing the biosensor cell illustrated in FIG. 7.

Referring to FIG. 8, in operation, once the known DNA 22 and unknown DNA 23 (with the fluorescent tag molecule attached thereto) are placed on the substrate (for example, each area corresponding to a given biosensor cell would have a distinct known DNA deposited thereon), after a predetermined period of time, the surface of the substrate is treated by the same process as discussed above to remove all DNA that does not hybridize. Then, the excitation light 83 is utilized to illuminate the substrate. Preferably, the entire substrate is illuminated at the same time. Utilizing the decoder 4, the output of each biosensor cell 2 is checked to determine if hybridization occurred between the known and unknown DNA sample deposited in the given biosensor cell 82 in the same manner as detailed above. The main difference of the embodiment of the present invention illustrated in FIGS. 7 and 8 is that the individual light source has been removed from the substrate, and a single light source 83 is utilized to illuminate the entire substrate. However, it is noted that because each biosensor cell is capable of making an independent determination regarding whether or not hybridization has occurred (i.e., each cell comprises detection circuitry), this embodiment also allows for the elimination of the timely and costly laser scanning procedures required by the prior art devices/techniques to detect hybridization. It is noted with regard to the biosensor chip 90, FIG. 8 merely illustrates the upper surface of the photodetection circuit 81 which forms the array of biosensor cells 82. While not shown in FIG. 8, the biosensor chip 90 would also contain the decoder 4, the A-to-D converter 3, the D-to-A converter 5 and the corresponding control circuitry, all formed in the monolithic semiconductor chip 90. FIG. 8 also illustrates the use of a data analyzer 91 (e.g., computer) to record the output of the biosensor chip 90.

In a variation to the embodiment illustrated in FIGS. 7 and 8, it is possible to place the known DNA and the unknown DNA (with the attached fluorescent tag molecule) on a glass (or transparent) substrate and then place the glass substrate on the chip (i.e., "bio-chip") containing the biosensor cells for processing. More specifically, in such a variation, the DNA would be placed on the glass substrate in an x-y array corresponding to the x-y array of biosensor cells contained in the biosensor chip. In other words, each "cell" of known and unknown DNA placed on the glass substrate would correspond to a given biosensor cell on the bio-chip. Once the glass substrate is placed on the bio-chip and properly aligned such that each known DNA sample (and unknown DNA sample) deposited on the glass substrate is positioned (i.e., aligned) over the predetermined biosensor cell, the glass substrate is illuminated and the processing to determine whether hybridization occurred proceeds as discussed above. This variation has the advantage that the known DNA and unknown DNA can be processed and treated (to remove the unhybridized DNA) without having to involve the "biochip", thereby simplifying the handling and processing procedures. However, as with the previous embodiment, this embodiment also allows for the elimination of the timely and costly laser scanning procedures required by the prior art devices/techniques to detect hybridization. This embodiment also allows for reuse of the sensor chip and disposal of the glass slide.

It is noted that the bio-chip utilized in the embodiment illustrated in FIGS. 7 and 8 can be substantially any photodetection device capable of generating a change in an electrical characteristic on the basis of the intensity of received light incident on the photodetector device. In addition, the photodetector device should be capable of differentiating a plurality of cells arranged in, for example, a x-y array. Possible devices for use as a photodetector, include but are not limited to, CCD arrays, CMOS sensor arrays, dedicated photodiode arrays, etc.

In yet another variation, the biosensor cell can be designed so as to include light filters so as to allow only the desired light (e.g., SYBR green) to be incident on the photodetector.

Figure 9:
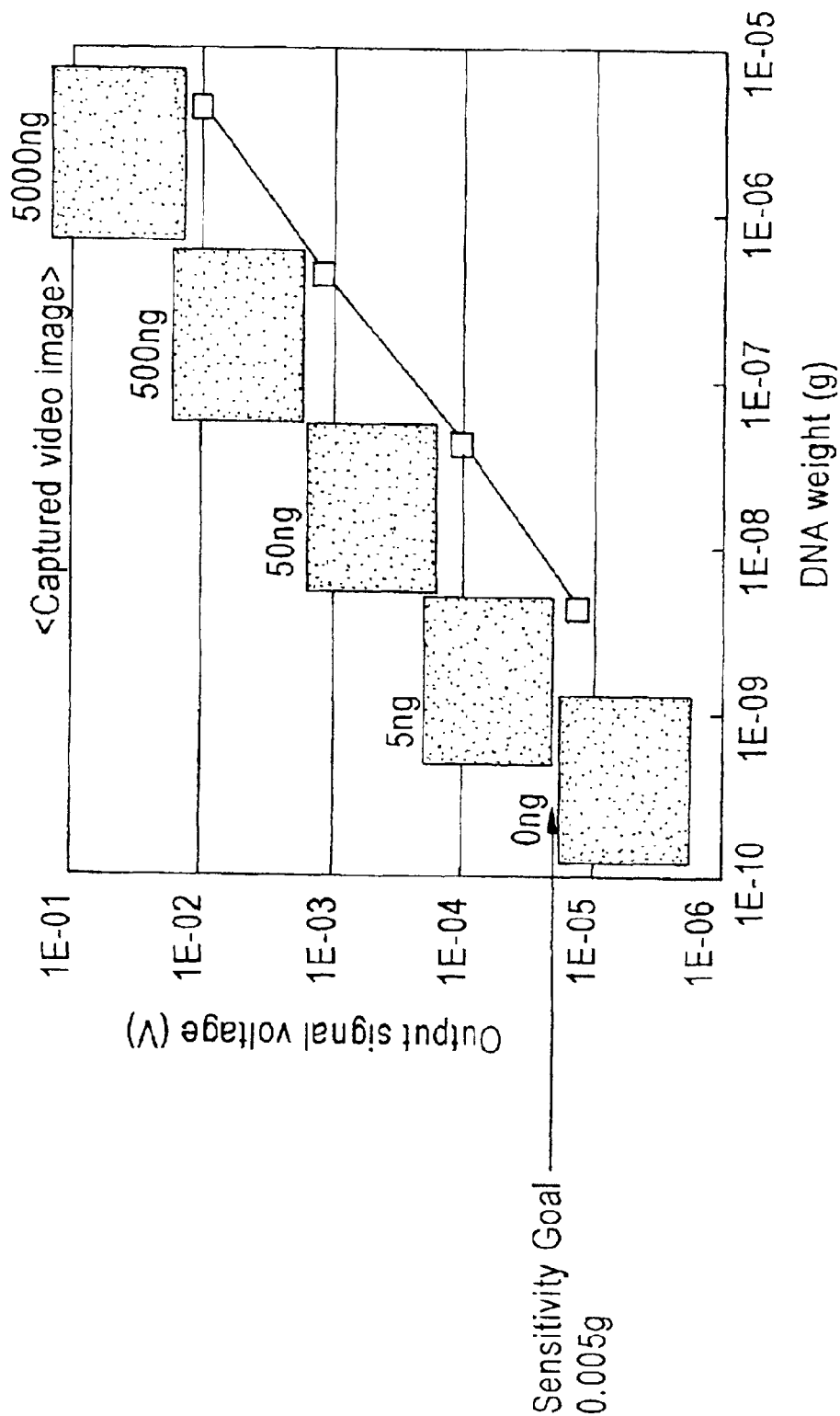
FIG. 9 illustrates exemplary measurements results regarding the detection of DNA.

FIG. 9 illustrates exemplary measurement results regarding the detection of DNA.

It is further noted that while the detection system of the present invention has been described with regard to identifying unknown DNA samples, it can also be utilized in conjunction with the identification of other chemical assays.

Although certain specific embodiments of the present invention have been disclosed, it is noted that the present invention may be embodied in other forms without departing from the spirit or essential characteristics thereof. The present embodiments are therefore to be considered in all respects as illustrative and not restrictive, the scope of the invention being indicated by the appended claims, and all changes that come within the meaning and range of equivalency of the claims are therefore intended to be embraced therein.

I claim:

1. An apparatus for identifying an unknown DNA sample, said apparatus comprising:
   a plurality of detection nodes, each of said detection nodes operable for allowing an interaction between a known DNA sample and an unknown DNA sample, and for generating an output signal if hybridization occurs between said known DNA sample and said unknown DNA sample; and
   a decoder operative for receiving an input signal indicative of which of said plurality of detection nodes should be selected for processing, and for outputting control signals which operate to activate said selected detection node;
   wherein each of said detection nodes includes a light source and a photodetection circuit, said photodetection circuit having a conductance value which varies if hybridization occurs between the known DNA sample and the unknown DNA sample deposited in said detection node, said change in said conductance value is operative for generating said output signal,
   wherein each detection node further comprises:
      a differential amplifier for receiving a first reference voltage signal and a second reference voltage signal as input signals, and for generating said output signal, said output signal representing a difference between said first reference voltage signal and said second reference voltage signal, wherein said first reference voltage signal varies in correspondence with changes in the conductance value of said photodetection circuit, and said second reference voltage signal is a constant value;
      a voltage supply coupled to said photodetection circuit by a resistive element, said change in the conductance value of said photodetection circuit causing an increase in current flow through said resistive element, said first reference voltage signal varying in correspondence with changes in said current flow through said resistive element;
      a first pass transistor operative for coupling said voltage supply to said resistive element and said light source; and
      a second pass transistor operative for coupling an output of said differential amplifier to an output port of said detection node,
      said first pass transistor and said second pass transistor being activated by said control signals output by said decoder.

2. The apparatus of claim 1, wherein said plurality of detection nodes are formed in a single monolithic semiconductor chip.

3. The apparatus of claim 1, wherein said output signal has an amplitude which varies in accordance with variations of said conductance value of said photodetection circuit.

4. The apparatus of claim 1, wherein each unknown DNA sample deposited in said detection node has a fluorescent tag molecule attached thereto.

5. The apparatus of claim 4, wherein hybridization of said known DNA sample and said unknown DNA sample results in the presence of said fluorescent tag molecule in said detection node, said fluorescent tag molecule receiving light from said light source and fluorescing, said photodetection circuit receiving light emitted from said fluorescent tag molecule, said photodetection circuit increasing said conductance value upon receiving light from said fluorescent tag molecule.

6. The apparatus of claim 5, wherein said increase in said conductance value of said photodetection circuit causes a corresponding reduction in the voltage level of said first reference voltage signal.

7. The apparatus of claim 1, wherein said photodetector circuit comprises a photodiode and said light source comprises a light-emitting diode.

8. A system for identifying an unknown DNA sample, said system comprising:
   a plurality of detection nodes, each of said detection nodes operable for allowing an interaction between a known DNA sample and an unknown DNA sample, and for generating an output signal if hybridization occurs between said known DNA sample and said unknown DNA sample, each of said detection nodes including a photodetection circuit, said photodetection circuit having a conductance value which varies if hybridization occurs between the known DNA sample and the unknown DNA sample deposited in said detection node, said change in said conductance value is operative for generating said output signal;
   a decoder operative for receiving an input signal indicative of which of said plurality of detection nodes should be selected for processing, and for outputting control signals which operate to activate said selected detection node; and
   a light source for illuminating said known DNA sample and said unknown DNA sample deposited in said detection node,
   wherein each detection node further comprises:
      a differential amplifier for receiving a first reference voltage signal and a second reference voltage signal as input signals, and for generating said output signal, said output signal representing a difference between said first reference voltage signal and said second reference voltage signal, wherein said first reference voltage signal varies in correspondence with changes in the conductance value of said photodetection circuit, and said second reference voltage signal is a constant value;
      a voltage supply coupled to said photodetection circuit by a resistive element, said change in the conductance value of said photodetection circuit causing an increase in current flow through said resistive element, said first reference voltage signal varying in correspondence with changes in said current flow through said resistive element;
      a first pass transistor operative for coupling the voltage supply to said resistive element and said light source; and
      a second pass transistor operative for coupling an output of said differential amplifier to an output port of said detection node,
      said first pass transistor and said second pass transistor being activated by said control signals output by said decoder.

9. The system of claim 8, wherein said plurality of detection nodes and said decoder are formed in a single monolithic semiconductor chip.

10. The system of claim 8, wherein said output signal has an amplitude which varies in accordance with variations of said conductance value of said photodetection circuit.

11. The system of claim 8, wherein each unknown DNA sample deposited in said detection node has a fluorescent tag molecule attached thereto.

12. The system of claim 11, wherein hybridization of said known DNA sample and said unknown DNA sample results in the presence of said fluorescent tag molecule in said detection node, said fluorescent tag molecule receiving light from said light source and fluorescing, said photodetection circuit receiving light emitted from said fluorescent tag molecule, said photodetection circuit increasing said conductance value upon receiving light from said fluorescent tag molecule.

13. The system of claim 12, wherein said increase in said conductance value of said photodetection circuit causes a corresponding reduction in the voltage level of said first reference voltage signal.

14. The system of claim 8, wherein said photodetector circuit comprises a photodiode and said light source comprises a light-emitting diode.

15. A system for identifying an unknown DNA sample, said system comprising:
 a substrate for receiving a plurality of known DNA samples and unknown DNA samples, each of said plurality of known DNA samples being located in a distinct area of said substrate, each distinct area of said substrate defining a cell;
 a plurality of detection nodes, each of said detection nodes including a photodetection circuit, said photodetection circuit having a conductance value which varies in accordance with the amount of light incident thereon, each of said detection nodes corresponding to a specific cell;
 a decoder operative for receiving an input signal indicative of which of said plurality of detection nodes should be selected for processing, and for outputting control signals which operate to activate said selected detection node; and
 a light source for illuminating said known DNA samples and said unknown DNA samples deposited on said substrate;
 wherein said substrate is aligned on top of said plurality of detection nodes such that each detection node is aligned with the corresponding cell, and if hybridization occurs between a known DNA sample and an unknown DNA sample deposited in a given cell on said substrate, the amount of light incident on said photodetection circuit of the detection node corresponding to said given cell changes, said detection node operative for generating an output signal indicating said change in incident light on said photodetection circuit,
 wherein each detection node further comprises:
  a differential amplifier for receiving a first reference voltage signal and a second reference voltage signal as input signals, and for generating said output signal, said output signal representing a difference between said first reference voltage signal and said second reference voltage signal, wherein said first reference voltage signal varies in correspondence with changes in the conductance value of said photodetection circuit, and said second reference voltage signal is a constant value;
  a voltage supply coupled to said photodetection circuit by a resistive element, said change in the conductance value of said photodetection circuit causing an increase in current flow through said resistive element, said first reference voltage signal varying in correspondence with changes in said current flow through said resistive element;
  a first pass transistor operative for coupling said voltage supply to said resistive element and said light source; and
  a second pass transistor operative for coupling an output of said differential amplifier to an output port of said detection node,
  said first pass transistor and said second pass transistor being activated by said control signals output by said decoder.

16. The system of claim 15, wherein said plurality of detection nodes and said decoder are formed in a single monolithic semiconductor chip.

17. The system of claim 15, wherein each unknown DNA sample deposited on said substrate has a fluorescent tag molecule attached thereto.

18. The system of claim 17, wherein hybridization of said known DNA sample and said unknown DNA sample results in the presence of said fluorescent tag molecule in said detection node, said fluorescent tag molecule receiving light from said light source and fluorescing, said photodetection circuit receiving light emitted from said fluorescent tag molecule, said photodetection circuit increasing said conductance value upon receiving light from said fluorescent tag molecule.

19. The system of claim 18, wherein said increase in said conductance value of said photodetection circuit causes a corresponding reduction in the voltage level of said first reference voltage signal.

20. The system of claim 15, wherein said photodetector circuit comprises a photodiode and said light source comprises a light-emitting diode.

* * * * *